(12) United States Patent
Arkatov et al.

(10) Patent No.: US 11,912,658 B2
(45) Date of Patent: Feb. 27, 2024

(54) METHOD FOR SEPARATING OLEFIN OLIGOMERIZATION PRODUCTS (VARIANTS)

(71) Applicant: PUBLIC JOINT STOCK COMPANY "SIBUR HOLDING", Tobolsk (RU)

(72) Inventors: Oleg Leonidovich Arkatov, Tomsk Tomskaya obl. (RU); Maxim Vladimirovich Lipskikh, Tomsk Tomskaya obl. (RU); Evgeniy Anatolievich Popov, Tomsk Tomskaya obl. (RU); Airat Faritovich Khusainov, Tomsk Tomskaya obl. (RU)

(73) Assignee: Public Joint Stock Company "Sibur Holding", Tobolsk (RU)

( * ) Notice: Subject to any disclaimer, the term of this patent is extended or adjusted under 35 U.S.C. 154(b) by 376 days.

(21) Appl. No.: 17/432,816

(22) PCT Filed: Feb. 22, 2019

(86) PCT No.: PCT/RU2019/000112
§ 371 (c)(1),
(2) Date: Aug. 20, 2021

(87) PCT Pub. No.: WO2020/171730
PCT Pub. Date: Aug. 27, 2020

(65) Prior Publication Data
US 2022/0127210 A1    Apr. 28, 2022

(51) Int. Cl.
*C07C 7/04* (2006.01)
*B01D 1/22* (2006.01)
(Continued)

(52) U.S. Cl.
CPC .............. *C07C 7/005* (2013.01); *B01D 1/222* (2013.01); *B01D 3/148* (2013.01); *B01J 31/143* (2013.01);
(Continued)

(58) Field of Classification Search
CPC ................................................. C07C 7/005–08
See application file for complete search history.

(56) References Cited

U.S. PATENT DOCUMENTS 7,718,838 B2    5/2010    Woodard et al.
2007/0161839 A1    7/2007    Woodard et al.
(Continued)

FOREIGN PATENT DOCUMENTS

| CN | 109265309 A | 1/2019 |
| RU | 2104088 C1 | 2/1998 |
| WO | 2015/179337 A1 | 11/2015 |

OTHER PUBLICATIONS

International Search Report and Written Opinion dated Oct. 31, 2019, directed to International Application No. PCT/RU2019/000112; 6 pages.
(Continued)

*Primary Examiner* — Jonathan Luke Pilcher
(74) *Attorney, Agent, or Firm* — Banner & Witcoff, Ltd.

(57) ABSTRACT

The invention relates to the field of olefin oligomerization to obtain liner α-olefins, particularly to a method of separating olefin oligomerization products using an evaporator. The invention includes two embodiments of the method of separating the oligomerization reaction product streams. In accordance with the first embodiment of the invention, the oligomerization reaction product stream after the step of isolating an initial olefin is fed into an evaporator to the step of separating the oligomerization reaction product steam. In accordance with the second embodiment of the invention,
(Continued)

the oligomerization reaction product stream after the step of isolating the initial olefin is separated into two streams, the first part of which is fed into the separation column, and the second part is fed into the evaporator. The invention allows to minimize a quantity of technological equipment contaminated by the by-product polymer.

21 Claims, 3 Drawing Sheets

(51) Int. Cl.
  *B01D 3/14* (2006.01)
  *B01J 31/14* (2006.01)
  *C07C 7/00* (2006.01)
  *C07C 11/107* (2006.01)

(52) U.S. Cl.
  CPC .............. *C07C 7/04* (2013.01); *C07C 11/107* (2013.01); *B01J 2231/20* (2013.01); *B01J 2531/62* (2013.01)

(56) References Cited

U.S. PATENT DOCUMENTS

2010/0036185 A1* 2/2010 Yokoyama ................ C07C 2/32
  585/510
2018/0179122 A1* 6/2018 Boutrot ................ B01J 19/2465

OTHER PUBLICATIONS

Nexant, Inc. (Apr. 2008). "PERP Report: Alpha Olefins 06/07-5," Nexant Chem Systems; 192 pages.

* cited by examiner

METHOD FOR SEPARATING OLEFIN OLIGOMERIZATION PRODUCTS (VARIANTS)

CROSS REFERENCE TO RELATED APPLICATIONS

This application is a U.S. national stage application under 35 U.S.C. § 371 of International Application No. PCT/RU2019/000112, filed Feb. 22, 2019, the entire contents of which is incorporated herein by reference.

FIELD OF THE INVENTION

The invention relates to the field of the oligomerization of olefins, in particular ethylene, to produce linear α-olefins, in particular hexene-1, used in the manufacture of a linear low-, medium- and high-density polyethylene, poly-α-olefins for drag-reducing additives, and the like. Particularly, the invention relates to a method of separating olefin oligomerization products using an evaporator.

BACKGROUND OF THE INVENTION

Patent U.S. Pat. No. 7,718,838 proposes several variants for the separation of a stream of oligomerization reaction products. Thus, one of the embodiments is a method of the separation that comprises discharging a reaction mass comprising a target product and by-products of the oligomerization reaction, ethylene, a catalyst system, from the oligomerization reactor. Then, the administration of a deactivating agent into the output line of the reaction mass from an oligomerization reactor is performed for the deactivation of the catalyst system. After this, the reaction mass comprising the deactivated catalyst system is fed into a separator for isolating an unreacted olefin. The reaction mass remaining after the isolation of the unreacted ethylene is fed into a separation column wherein the reaction mass is separated into three streams: a stream of the target oligomerization product, a stream of a solvent and a stream of heavy products, including by-products of the oligomerization reaction, for example, C10 olefins, the by-product polymer, and also the deactivated catalyst system. At the same time, the stream of heavy products may be fed into an additional separation column to isolate C10 olefins.

In this method there is the necessity to clean out an equipment from the by-product polymer periodically, and also to control a molecular weight of the by-product polymer accurately, since a low molecular by-product polymer can form sediments in the equipment.

Application WO2015179337 also discloses a method for separating an oligomerization reaction product stream comprising the discharge of a reaction mass from the oligomerization reactor followed by administering a deactivating agent into the output line of the reaction mass from the oligomerization reactor to deactivate the catalyst system. Then, the reaction mass comprising the deactivated catalyst system is fed into a first separation device, for example, a separation column or an evaporator, to obtain three streams: a light stream comprising ethylene and butene-1, a target product stream comprising hexene-1 and/or octene-1, and also a solvent, and a heavy stream comprising heavy C10+ oligomers, a by-product polymer and the deactivated catalyst system. Thereafter, the heavy stream is fed into a second separation device, for example, into a thin-film evaporator, in which the separation of the heavy stream into a stream predominantly comprising heavy liquid C10+ oligomers and a stream predominantly comprising the by-product polymer and the deactivated catalyst system is occurred.

In accordance with the method, the whole stream, including the stream comprising the by-product polymer and the deactivated catalyst system, is fed into the separation column. The presence of the deactivated catalyst system and by-product polymer in the stream may result in the deposition thereof on walls of the equipment, and also in the increase in power inputs to separate the whole product.

Furthermore, the state of the art (PERP Report Alpha Olefins 06/07-5, Nexant Inc., 2008, pp. 81-82) discloses a method of separating products of the ethylene oligomerization that comprises the following steps:
a) discharging a reaction mass comprising a solvent, for example, cyclohexane, unreacted ethylene, hexene-1, C10+ olefins, catalyst system components and a by-product polymer, from an oligomerization reactor;
b) feeding the reaction mass of step a) into a separator, wherein there is the isolation of a major part of unreacted ethylene followed by recycling it into the oligomerization reactor;
c) the stream remaining after the isolation of ethylene in step b) is treated with the deactivating agent, for example, 2-ethylhexanol, for deactivating the catalyst system;
d) the stream obtained in step c), comprising hexene-1, C10+ olefins, a solvent, a deactivated catalyst system and a by-product polymer, is fed into the separation column, wherein it is separated into two streams: an upper stream comprising hexene-1 and a solvent, for example, cyclohexane, and a bottom stream comprising C10+ olefins, a by-product polymer and a deactivated catalyst system;
e) the upper stream of step d) comprising hexene-1 and solvent, for example, cyclohexane, is fed into the solvent separation column, wherein the separation of the solvent from a fraction predominantly comprising hexene-1 occurs;
f) the fraction predominantly comprising hexene-1 of step e) is directed to the isolation of hexene-1;
g) the bottom stream of step d) comprising C10+ olefins, the by-product and the deactivated catalyst system is fed into the column for separating a fraction predominantly comprising C10 olefins, to obtain a heavy fraction comprising the by-product polymer and the deactivated catalyst system.

The drawback of the method is the later feeding of the catalyst system deactivating agent, which results in increasing the risk of sedimentation of reaction by-products in the system before feeding the deactivating agent.

Thus, methods of separating the stream of olefin oligomerization products known from the art are insufficiently effective and are concurrently expensive and energy-consuming.

In view of this, one perspective direction is the development of the effective method for separating olefin oligomerization reaction product stream that is characterized by a good-quality and complete deactivation of the catalyst system to reduce proceeding side reactions outside the reaction zone, the preliminary concentration of the by-product polymer and the removal thereof from the system to exclude the formation of sediments in the equipment and reduce power inputs for the separation.

SUMMARY OF THE INVENTION

It is an object of the present invention to develop the effective method for separating olefin oligomerization reaction products allowing to minimize a quantity of technological equipment contaminated by a by-product polymer.

The technical result resides in the exclusion of the presence of the by-product polymer in a target product and a recurrent solvent isolation unit, and also in the maximal extraction of the target product and the solvent from a reaction mass, and in the obtainment of a heavy fraction (the fraction of products with higher oligomerization degree), in particular, C8+ fraction purified from the catalyst system components and the by-product polymer, which in turn allows to use a C8+ fraction for washing the oligomerization reactor.

The additional technical result is the exclusion of ingress of the catalyst system deactivating agent into the recurrent solvent.

The technical problem is solved and the achievement of the technical result is provided due to the realization of the method for separating the olefin oligomerization reaction product stream wherein one of the steps is performed in an evaporator.

In accordance with the first embodiment of the present invention, a method of separating olefin oligomerization products is proposed, which comprises the following sequence of steps:
  a) discharging a reaction mass from an oligomerization reactor;
  b) contacting the reaction mass with a catalyst system deactivating agent;
  c) isolating a fraction comprising an initial olefin from the reaction mass to form an oligomerization reaction product stream;
  d) separating, in an evaporator, of the oligomerization reaction product stream into a fraction predominantly comprising a target α-olefin and a fraction comprising a by-product polymer and residues of the catalyst system components,
  e) separating the fraction predominantly comprising the target α-olefin obtained in step d) into a light fraction, in particular C2-C4 fraction, a fraction of the target α-olefin, in particular C6+ fraction, and a heavy fraction of oligomers, in particular C8+ fraction.

In accordance with the second embodiment of the present invention, a method of separating olefin oligomerization products is proposed, which comprises the following sequence of steps:
  a) discharging a reaction mass from an oligomerization reactor;
  b) contacting the reaction mass with a catalyst system deactivating agent;
  c) isolating a fraction comprising an initial olefin, in particular ethylene, from the reaction mass to form an oligomerization reaction product stream;
  c)* directing a first part of the oligomerization reaction product stream from step c) into the separation step d)*; and directing a second part of the oligomerization reaction product stream from step c) into step d);
  d)* separating the first part of the oligomerization reaction product stream from step c)* into a light fraction, in particular C2-C4 fraction, a fraction of a target α-olefin, in particular C6+ fraction, and a heavy fraction of oligomers, in particular C8+ fraction, followed by directing the heavy fraction of oligomers, in particular, C8+ fraction, into step d);
  d) separating, in the evaporator, the heavy fraction of oligomers, in particular, C8+ fraction from step d)* and the second part of the oligomerization reaction product stream into a fraction predominantly comprising a target α-olefin, in particular C6+, and a fraction comprising a by-product polymer and residues of the catalyst system components;
  e) separating the fraction predominantly comprising the target α-olefin, in particular C6+, obtained in step d) into a light fraction, in particular C2-C4 fraction, a fraction of the target α-olefin, in particular C6+ fraction, and a heavy fraction of oligomers, in particular, C8+ fraction.

The present invention allows to minimize the quantity of technological equipment contaminated by the by-product polymer.

DESCRIPTION OF DRAWINGS

FIG. 1 shows a block diagram showing a sequence of steps in accordance with the first embodiment of the present invention.

FIG. 2 shows a block diagram showing a sequence of steps in accordance with the second embodiment of the present invention.

FIG. 3 shows a block diagram showing a sequence of steps in accordance with the comparative Example 3.

DETAILED DESCRIPTION OF THE INVENTION

Figure 1:
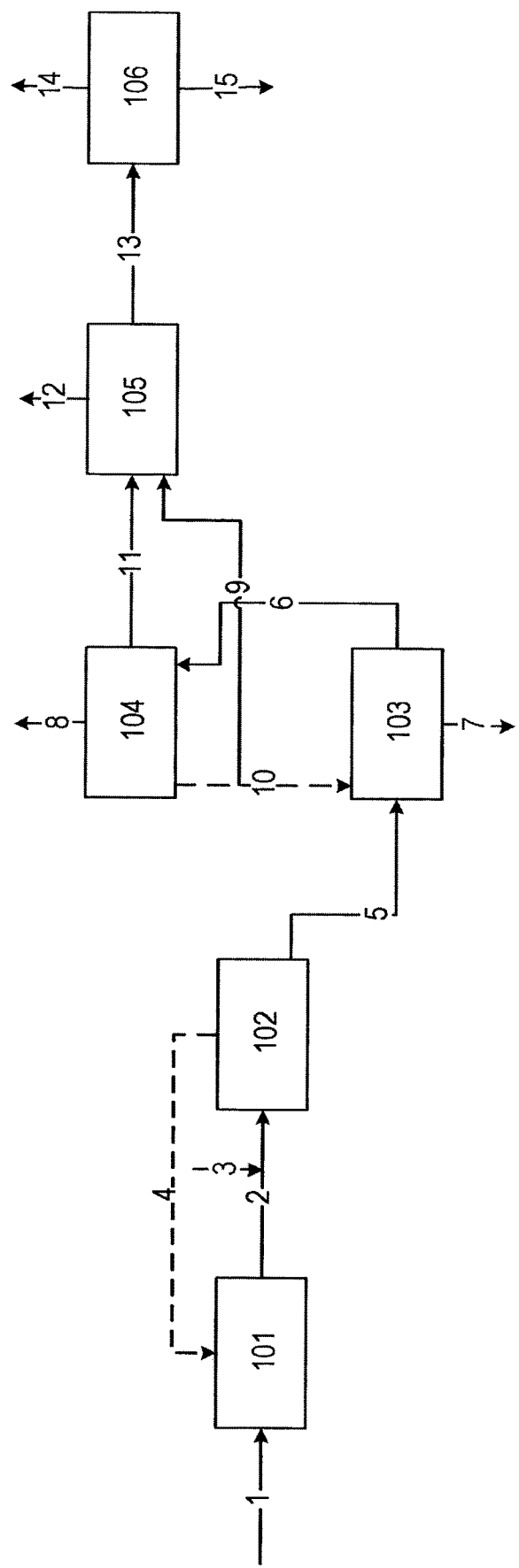
FIG. 1, FIG. 2 and FIG. 3 are presented to elucidate technical solutions disclosing the essence of the present invention.

The description of various aspects of the realization of the present invention is further presented.

In accordance with the present invention, the process of oligomerization of olefins comprises interacting, under oligomerization conditions, a raw material comprising an initial olefin with a catalyst system that comprises 1) a chromium source; 2) a nitrogen-containing ligand; and 3) an alkylaluminum, and optionally a zinc compound.

In accordance with the present invention, the chromium source can be organic and/or inorganic chromium compounds. The oxidation state of chromium in compounds may vary and may be +1, +2, +3, +4, +5 and +6. In the general case, the chromium source is the compound with the general formula $CrX_n$, wherein X may be the same or different, and n may represent an integer from 1 to 6. X may be organic or inorganic groups.

Organic groups X may have from 1 to 20 carbon atoms and represent an alkyl group, an alkoxy group, a carboxyl group, an acetylacetonate group, an amino group, an amido group, and the like.

Suitable inorganic groups X are halogenides, sulfates and the like.

Examples of chromium sources include: chromium (III) chloride, chromium (III) acetate, chromium (III) 2-ethylhexanoate, chromium (III) acetylacetonate, chromium (III) pyrrolide, chromium (II) acetate, chromium (IV) dioxide dichloride ($CrO_2Cl_2$) and the like.

The nitrogen-containing ligand composing the catalyst system is an organic compound comprising a pyrrole ring moiety, i.e. a five-membered aromatic ring with one nitrogen atom. Suitable nitrogen-containing ligands are pyrrole, 2,5-dimethylpyrrole, lithium pyrrolide $C_4H_4NLi$, 2-ethylpyrrole, 2-allylpyrrole, indole, 2-methylindole, 4,5,6,7-tetrahydroindole, but are not limited to the recited ones. The use of pyrrole or 2,5-dimethylpyrrole is the most preferable.

Alkylaluminum may represent an alkylaluminum compound, and also a halogenated alkylaluminum compound, an alkoxyalkylaluminum compound, and mixtures thereof. In order to increase the selectivity of the catalyst system, it is preferable to use these compounds that have not been in contact with water (not hydrolyzed), represented by general formulas AlR3, AlR2X, AlRX2, AlR2OR, AlRXOR and/or Al2R3X3, wherein R is an alkyl group, X is a halogen atom. Suitable alkylaluminum compounds are, but are not limited to: triethylaluminum, diethylaluminum chloride, tripropylaluminum, triisobutylaluminum, diethylaluminum ethoxide and/or ethylaluminum sesquichloride or mixtures thereof. The use of triethylaluminum or a mixture of triethylaluminum and diethylaluminum chloride is the most preferable.

According to the present invention, said catalyst system may be obtained by mixing a chromium source and a nitrogen-containing ligand in a hydrocarbon solvent, followed by mixing them with alkylaluminum. In this case, it is preferable to additionally activate alkylaluminum using a microwave irradiation, such as for instance UHF- or SHF-irradiation.

Mixing of the catalyst system components may be accomplished by any method known in the art. The mixing of the catalyst system components is performed for from 1 minute to 30 minutes, preferably not less than 2 minutes, not less than 4 minutes, not less than 8 minutes, not less than 15 minutes, or not less than 25 minutes.

Alternatively, alkylaluminum, which is subjected to the activation by microwave irradiation, may be gradually fed into mixing with other catalyst system components directly from the vessel subjected to the microwave radiation, so that the mixing time may be any convenient time without the loss of special properties acquired by components under exposure to the microwave irradiation.

The catalyst system components may be mixed in any order. Preferably, alkylaluminum is added to the mixture of the chromium source and the nitrogen-containing ligand. The mixing of components is performed in the presence of a hydrocarbon solvent in any suitable device known from the prior art, for example, in a bubble apparatus, an apparatus provided with a stirrer, a static mixer.

Suitable hydrocarbon solvents are, but are not limited to: hexene-1, benzene, toluene, ethylbenzene, xylene, or mixtures thereof. Preferably, aromatic hydrocarbons are used as a solvent, these hydrocarbons promote an increase in the stability of the catalyst system and the preparation of the highly active and selective catalyst system. Preferably, the aromatic hydrocarbon solvent is selected from the group consisting of toluene, ethylbenzene, or mixtures thereof. The most preferred aromatic hydrocarbon is ethylbenzene.

After the step of mixing and obtaining the catalyst system, it is possible to remove the hydrocarbon solvent from the mixture. As it is known from the art (for example, patent RU2104088), the presence of an aromatic hydrocarbon in the reaction mixture during the oligomerization process can reduce the activity of the catalyst system and increase the amount of by-products, such as polymers. The removal of the solvent can be performed by any known method, for example, by creating the rarefaction (vacuuming). However, it should be noted that the removal of the solvent is not always required. Thus, in the case of carrying out the olefin oligomerization process at elevated temperatures, the presence of an unsaturated hydrocarbon solvent (for example, ethylbenzene) may be preferable, since the indicated solvent increases the stability of the catalyst system at elevated temperatures.

The microwave irradiation exposure of alkylaluminum may be carried out both in the form of the compound itself, preferably in a liquid aggregate state, and in the form of a solution in the hydrocarbon solvent, for example, in hexane, cyclohexane, C10-C12 hydrocarbon fractions.

During the radiation exposure, it is necessary that the catalyst system components subjected to the activation are placed into a vessel that is transparent to the microwave irradiation, for example, into the vessel made of glass, fluoroplastic, and polypropylene.

The microwave irradiation used can have a frequency in the range of from 0.2 to 20 GHz. The use of the microwave irradiation with a frequency of 2.45 GHz not causing radiointerference and widely used in household and industrial sources of the microwave irradiation is especially preferable.

The nominal microwave irradiation power is from 1 to 5000 W per 1 g of the used aluminum alkyl in terms of elementary aluminum.

To achieve the best results, it is preferable that the irradiation time will be from 20 seconds to 20 minutes, preferably 15 minutes. The time of the exposure of more than 20 minutes usually does not provide additional advantages for the properties of the obtained catalyst system. The time of the exposure of less than 20 seconds may be insufficient to provide the significant alteration of properties of the components subjected to the activation, which in turn results in an insufficient increase in the activity and/or selectivity of the resulting catalyst system.

The mixing of alkylaluminum activated by microwave irradiation (microwave irradiation) with a chromium source and a nitrogen-containing ligand is carried out for not more than 3 minutes after the termination of the exposure, preferably not more than 1 minute after the termination of the exposure.

If the period of time between mixing the irradiated alkylaluminum with the chromium source and the nitrogen-containing ligand is 3 minutes or more, the properties of the resulting catalyst system significantly deteriorate as compared to the system in which the indicated period of time is less than 1 minute.

Ratios of the catalyst system components may vary. The aluminum:chromium molar ratio may be from 5:1 to 500:1, preferably from 10:1 to 100:1, most preferably from 20:1 to 50:1. The ligand:chromium molar ratio may vary from 2:1 to 50:1, preferably from 2.5:1 to 5:1.

As it is indicated above, the olefin oligomerization process in accordance with the present invention may be carried out by interacting under conditions of the oligomerization a raw material comprising an initial olefin in the presence of a catalyst system and optionally a zinc compound.

The zinc compound may be used both in the form of an individual compound and in the mixture with other compounds, for example, in the form of a solution in hydrocarbons.

The zinc compound or the mixture of these compounds may be directly added into the catalyst system at the step of the preparation thereof or independently into the oligomerization reactor.

The zinc compound is used as an additional activator of a catalyst centre, in particular, of the chromium. The zinc compound is preferably used in the absence of the visible radiation and UV-radiation in order to increase stability thereof.

The zinc compound may represent a metal zinc, a zinc-copper couple, activated zinc, alkyl zinc compounds, in particular dimethyl-, diethyl- and dibutyl zinc, aryl zinc compounds such as diphenyl- and ditolyl zinc, zinc amides, in particular zinc pyrrolides and zinc porphyrin complexes, zinc oxygenates (including formate, acetate, hydroxide acetate, 2-ethylhexanoate and other zinc carboxylates), zinc halides, in particular, anhydrous zinc chloride, or combinations thereof. It is preferable to use zinc compounds soluble in solvents used in the oligomerization process.

The zinc:chromium ratio may vary and can be of from 2:1 to 100:1, preferably from 5:1 to 50:1.

The catalyst system prepared in accordance with the present invention is fed into the oligomerization reactor by any method known in the art, in a diluted or undiluted form. It is preferable to perform the dilution of the catalyst system with a hydrocarbon diluent. For reasons set forth above, it is especially preferable to use the dilution with the saturated hydrocarbon solvents or with a mixture thereof. However, it is preferable that the content of aromatic compounds does not exceed 2 wt. %.

A hydrocarbon solvent, such as e.g. alkane, cycloalkane, a mixture of different alkanes and/or cycloalkanes, is used as a solvent in the oligomerization process. The hydrocarbon solvent may also comprise unsaturated hydrocarbons, such as olefins or aromatic compounds. Suitable hydrocarbon solvents or solvent components are heptane, cyclohexane, decane, undecane, an isodecane fraction, hexene-1. Preferably, heptane, cyclohexane, undecane are used as the solvent; more preferably, cyclohexane or heptane are used.

As the initial olefin in the olefin oligomerization process, olefins represented by ethylene (ethene), propylene (propene) and butylene (butene) are used. Preferably, ethylene (ethene) is used as the initial olefin.

The olefin oligomerization process is carried out to produce oligomerization products, namely higher olefins. The industrially important processes are processes of producing the oligomerization products, such as α-olefins, from ethylene. The α-olefins are compounds with a double carbon-carbon (C=C) bond in the α-position.

The α-olefins obtained in the oligomerization process may comprise different C4-C40 olefins and mixtures thereof. For example, α-olefins obtained in the ethylene oligomerization process may represent butene-1, hexene-1, octene-1, decene-1, dodecene-1, higher α-olefins, or mixtures thereof. Preferably, the oligomerization process is the process of ethylene trimerization to obtain a target α-olefin, namely hexene-1.

The oligomerization process may be performed in any reactors known in the art. Suitable reactors are a continuous stirred reactor, a batch reactor, a plug flow reactor, and a tubular reactor. The reactor can be a gas-liquid reactor, for example, an autoclave with a stirrer, a bubble column (bubble reactor) with a feeding gas and liquid as co-current or counter-current flow, and also a bubble gas lift reactor.

In the preferred embodiment of the method, when the oligomerization process is the ethylene trimerization process to produce hexene-1, the ethylene pressure varies in the range of from 1 to 200 atm, preferably from 10 to 60 atm, most preferably from 15 to 40 atm. Increasing the pressure of ethylene for accelerating the oligomerization rate is preferable.

The temperature of the oligomerization process can vary in the range of from 0 to 160° C., preferably from 40 to 130° C. It is the most preferable to maintain the temperature in the reactor in the range of from 80 to 120° C. At this temperature, the by-product polymer, in particular polyethylene, will not precipitate from the solution, i.e. will be removed from the reactor in the form of a solution, and the catalyst system will be most active and selective. Performing the oligomerization process at higher temperatures (above 160° C.) may result in the deactivation of the catalyst system.

In accordance with the proposed method, the reaction time may vary. The reaction time can be defined as the residence time of the raw material and the solvent in the reaction zone of the oligomerization. When using continuous-flow tank reactors, the reaction time can be defined as an average residence time. The reaction time may vary depending on the olefin used as the raw material, the reaction temperature, the pressure and other parameters of the process. In the embodiments of the method, the reaction time does not exceed 24 hours. The reaction time may be less than 12 hours, less than 6 hours, less than 3 hours, less than 2 hours, less than 1 hour, less than 30 minutes, less than 15 minutes, less than 10 minutes. The most preferred reaction time is from 30 minutes to 90 minutes.

According to the proposed method, olefin and the catalyst system can contact with hydrogen that is fed into the oligomerization reactor and is used as a diluent. Hydrogen can accelerate the oligomerization reaction and/or increase the activity of the organometallic catalyst. Furthermore, hydrogen may result in a decrease in the amount of polymer produced as the by-product and thereby limit the deposition of the by-product polymer on walls of the equipment.

The olefin oligomerization process is performed in the absence of water and oxygen.

The initial olefin, the solvent and the catalyst system may be introduced into the oligomerization reactor in any order. Preferably, the components are introduced in the following sequence: the solvent, then the catalyst system, followed by dosing the initial olefin.

In accordance with the present invention, the reaction mass leaving the reactor may contain an initial olefin, a catalyst system, a target α-olefin, which is the target oligomer of the initial α-olefin, by-products, a solvent, and also a by-product polymer that may be formed during the oligomerization process.

The target α-olefin may comprise isomers of the target α-olefin, and a weight ratio of the target α-olefin to corresponding isomers should be at least 99.5:0.5.

The reaction mass leaving the reactor in step b) contacts with a catalyst system deactivating agent to produce the reaction mass comprising residues of the catalyst system.

Suitable catalyst system deactivating agents known in the art are water, alcohols, amines, amino alcohols, or mixtures thereof, and also various sorbents, such as silica gel, alumina, aluminosilicates, or mixtures thereof with water, alcohols, amines, and amino alcohols. As alcohols, for example, methanol, ethanol, n-propanol, isopropanol, n-butanol, isobutanol, tert-butanol, 2-ethylhexanol, ethylene glycol, propylene glycol, triethylene glycol, polyethylene glycol or mixtures thereof may be used. Examples of suitable amines are ammonia, methylamine, dimethylamine, trimethylamine, ethylamine, diethylamine, triethylamine, tri-n-propylamine, diisopropylethylamine, tri-n-butylamine, piperazine, pyridine, ethylene diamine, diethylenetriamine, or mixtures thereof. Examples of amino alcohols include ethanolamine, diethanolamine, triethanolamine, methyldiethanolamine, dodecyl diethanolamine, 1-amino-2-propanol, or mixtures thereof.

Preferably, alcohols or amino alcohols such as 2-ethylhexanol, ethylene glycol, propylene glycol, diethanolamine, triethanolamine, more preferably 2-ethylhexanol are used as the catalyst system deactivating agent The administration of the catalyst system deactivating agent is performed in the output line of the reaction mass from the oligomerization reactor. Preferably, the entry point of the deactivating agent is located near the oligomerization reactor. The indicated output line of the reaction mass from the oligomerization reactor should have a minimum number of stagnant zones, a reduced hydraulic resistance to increase the efficiency of the deactivation of the catalyst system in order to avoid the precipitation of a by-product polymer. Alternatively, the catalyst system deactivating agent may be introduced into the apparatus, in which step c) of isolating the fraction containing the initial olefin from the reaction mass is performed After the deactivation of the catalyst system, the reaction mass containing residues of the catalyst system enters the step c) of isolating the initial olefin.

In step c), a light fraction containing the initial olefin is isolated from the reaction mass containing residues of the catalyst system to form the oligomerization reaction product stream.

The isolation from the reaction mass of the light fraction containing the initial olefin, is carried out in any suitable equipment known from the prior art. Examples of such equipment are, but are not limited to, batch or continuous settlers, for example, settlers with the overflow wall. Size and shape of the settler depends on the concentration of the suspension of the by-product polymer and the deposition rate.

The settling rate depends on a temperature, since while the temperature of the suspension of the by-product polymer changes, its viscosity changes.

The isolation process is carried out at a temperature of from 60 to 120° C., preferably from 70 to 110° C., more preferably at a temperature of from 80 to 110° C., and a pressure of from 0 to 60 atm, preferably from 0 to 40 atm, more preferably from 0 to 30 atm.

The fraction comprising the initial olefin isolated in step c) may also comprise C4 fraction comprising butene-1 and butene-2 in an amount of not more than 2 wt. %, preferably not more than 1 wt. %, more preferably not more than 0.03 wt. %.

The fraction comprising the initial olefin isolated in step c) may be recycled into the oligomerization reactor.

The stream of oligomerization products may also be settled in step c), upon which the concentrating of the by-product polymer and residues of the catalyst system on the bottom of the settler is observed to produce a clarified part of the oligomerization reaction products, said part containing a small amount of the catalyst system and the by-product polymer, and a concentrated part of the oligomerization reaction products containing the main part of the by-product polymer and the catalyst system residues.

In accordance with the first embodiment of the present invention, the stream of oligomerization reaction products from step c) is directed to step d) of separating the stream of oligomerization reaction products into a fraction predominantly comprising oligomers, in particular C6+, and a fraction comprising a by-product polymer and catalyst system residues.

In accordance with the present invention, the step d) of separating is carried out in an evaporator. The evaporator may be, but is not limited to, a vertical apparatus, such as a film evaporator, and a rotary film evaporator. Preferably, the rotary film evaporator is used.

The separation process in the evaporator is carried out at a temperature of from 64 to 175° C., more preferably at a temperature of from 80 to 150° C., and a pressure of from 0 to 6 atm gauge, preferably from 0 to 3 atm gauge, more preferably from 0 to 2 atm gauge The fraction obtained in step d) predominantly containing oligomers, in particular C6+, includes the target α-olefin, preferably hexene-1, in an amount of from 20 to 25 wt. %, residues of the light fraction, in particular, the C2-C4 fraction, in an amount of not more than 1 wt. %, a solvent in an amount of from 73 to 79 wt. %, and the heavy fraction, in particular the C8+ fraction in an amount of not more than 2 wt. %.

The fraction obtained in step d), containing the by-product polymer and the catalyst system residues, is a suspension of the by-product polymer and the catalyst system residues suspended in the oligomerization reaction products, and it also contains the catalyst system deactivating agent.

After the separation, the fraction predominantly containing C6+ is directed to step e) for separating into three fractions: a light fraction, in particular the C2-C4 fraction, a fraction of the target α-olefin, in particular the C6+ fraction, and a heavy fraction of oligomers, in particular the C8+ fraction Step e) is carried out in any suitable apparatus known from the prior art. Examples of such apparatuses are, but are not limited to, an evaporation column, a separation column equipped with various types of contact devices.

The separation process in step e) is carried out at a temperature of from 64 to 140° C., more preferably at a temperature of from 64 to 120° C., and a pressure of from 0 to 4 atm, preferably from 0 to 3 atm, more preferably from 0 to 2 atm.

The light fraction obtained in step e), in particular the C2-C4 fraction, includes the initial olefin, preferably ethylene, butene-1 and butene-2. The indicated light fraction, in particular C2-C4, is returned to the oligomerization reactor if necessary.

The fraction of the target α-olefin obtained in step e), in particular the C6+ fraction, includes the target α-olefin, preferably hexene-1, in an amount of from 21 to 27 wt. %, and a solvent. The fraction of the target α-olefin (in particular, the C6+ fraction) also comprises C8 olefins in an amount of 0.25 wt. % and C10 olefins in an amount of not more than 0.5 wt. % The oligomer fraction (C6+ fraction) is then directed to the isolation step of the target α-olefin, preferably hexene-1.

The heavy fraction of oligomers obtained in step e), in particular C8+ fraction, comprises C8 olefins, including octene-1, C10 olefins, in particular decenes.

The heavy fraction of oligomers (in particular, the C8+ fraction) is then directed to the isolation step of the target α-olefin together with the fraction of the target α-olefin (in particular, C6+ fraction) or to the isolation step of the target α-olefin and to the evaporator in step d).

The step of isolating the target α-olefin is carried out in a packed or plate-type distillation column. The content of the target α-olefin in the fraction of the target α-olefin, preferably hexene-1, is at least 95 wt. %, preferably 97 wt. %, more preferably 99 wt. %. The bottom product left after the isolation of the target α-olefin is directed to the step of solvent isolation.

The step of the solvent isolation is carried out in a nozzle or disc distillation column. Preferably, the solvent isolated at this step is recycled to the reactor (recurrent solvent). The purity of the recurrent solvent is at least 90%, preferably at least 95%, more preferably at least 99%.

The bottom product of the isolation step of the recurrent solvent is a heavy fraction of oligomers (in particular, the C8+ fraction) predominantly comprising octenes in an amount of from 95 to 99 wt. %, decenes in an amount of from 0.5 to 4.7 wt. % and a solvent in an amount of not more than 2 wt. %. Furthermore, the indicated bottom product may comprise a small amount of the catalyst system deactivating agent, the amount of which should not exceed 0.005 wt. %, preferably 0.002 wt. %, more preferably 0.0005 wt.

%. The indicated heavy fraction of oligomers (C8+ fraction) may be used for washing the reaction equipment for cleaning it from the sediment of the by-product polymer and the catalyst system residues.

In accordance with the second embodiment of the present invention, the stream of the oligomerization reaction products from step c) is directed to step c*), in which the first part of the stream of the oligomerization reaction products is directed from step c) to the separation step d)*; and the second part of the stream of the oligomerization reaction products is directed from step c) to step d).

At step d)*, the separation of the first part of the stream of the oligomerization reaction products from step c)* into a light fraction, in particular the C2-C4 fraction, a fraction of the target α-olefin, in particular the C6+ fraction, and a heavy fraction of oligomers, in particular fraction C8+ followed by directing the heavy fraction (in particular the C8+ fraction) to step d).

In accordance with the present invention, step d)* is carried out together with step e).

Steps d)* and e) are carried out in any suitable apparatus known from the prior art. Examples of such devices are, but are not limited to, an evaporation column, a separation column equipped with various types of contact devices.

The separation process in steps d)* and e) is carried out at a temperature of from 64 to 140° C., more preferably at a temperature of from 64 to 120° C., and a pressure of from 0 to 4 atm gauge, preferably from 0 to 3 atm gauge, more preferably from 0 up to 2 atm gauge.

The light fraction obtained in steps d)* and e), in particular the C2-C4 fraction, includes the initial olefin, preferably ethylene, as well as butene-1 and butene-2. The light fraction (in particular, the C2-C4 fraction) is recycled to the oligomerization reactor as needed.

The fraction of the target α-olefin obtained in steps d)* and e), in particular the C6+ fraction, includes the target α-olefin, preferably hexene-1 in an amount of from 21 to 27 wt. %, and a solvent. The C6+ fraction also contains C8 olefins in the amount of 0.25 wt. % and C10 olefins in the amount of not more than 0.5 wt. %. The fraction of the target α-olefin (in particular, the C6+ fraction) is then directed to the isolation step of the target α-olefin, preferably hexene-1.

The heavy fraction of oligomers obtained in steps d)* and e), in particular the C8+ fraction, contains C8 olefins, including octene-1, C10 olefins, in particular, decenes. The heavy fraction of oligomers (in particular, the C8+ fraction) is then directed to the isolation step of the target α-olefin or to the isolation step of the target α-olefin and to an evaporator of step d).

In accordance with the present invention, the separation step d) is carried out in an evaporator. The evaporator may be, but is not limited to, vertical apparatus, such as a film evaporator, a rotary film evaporator. Preferably, the rotary film evaporator is used.

The separation process in the evaporator is carried out at a temperature of from 64 to 175° C., more preferably at a temperature of from 80 to 150° C., and a pressure of from 0 to 6 atm, preferably from 0 to 3 atm, more preferably from 0 to 2 atm.

The fraction of the target α-olefin obtained in step d), in particular the fraction predominantly containing C6+, includes the target oligomer of α-olefin, preferably hexene-1 in an amount of from 20 to 25 wt. %, residues of the light fraction, preferably the C2-C4 fraction, in an amount of not more than 1 wt. %, a solvent in an amount of from 73 to 79 wt. %, and a heavy fraction of oligomers (in particular, the C8+ fraction) in an amount of not more than 2 wt. %.

The fraction obtained in step d), containing the by-product polymer and the catalyst system residues, is a suspension of the by-product polymer and the catalyst system residues suspended in the oligomerization reaction products, and also contains the catalyst system deactivating agent.

After the separation, the fraction of the target α-olefin, in particular, the fraction predominantly containing C6+, is directed to step e) to be separated into three fractions: a light fraction, in particular the C2-C4 fraction, a fraction of the target α-olefin, in particular the C6+ fraction, and a heavy fraction of oligomers, in particular the C8+ fraction.

The isolation step of the solvent is carried out in a packed or plate-type distillation column. Preferably, the solvent isolated at this step is recycled to the reactor (recurrent solvent). The purity of the recurrent solvent is at least 90%, preferably at least 95%, more preferably at least 99%.

The bottom product of the isolation step of the recurrent solvent is a heavy fraction of oligomers (in particular, the C8+ fraction) predominantly containing octenes in an amount of not more than 17 wt. %, decenes in an amount up to 81 wt. % and a solvent in an amount of not more than 2 wt. %. Furthermore, the indicated bottom product may contain a small amount of the catalyst system deactivating agent, the amount of which should not exceed 0.005 wt. %, preferably 0.002 wt. %, more preferably 0.0005 wt. %. The indicated C8+ fraction can be used to wash the reaction equipment in order to clean it of sediments of the by-product polymer and the catalyst system residues.

In more detail, one of the embodiments of the present invention is explained in FIG. 1, which presents a flowchart of the olefin oligomerization process with the implementation of the method of separating the oligomerization products according to the first embodiment of the present invention. In accordance with FIG. 1, 101 is an oligomerization reactor, 102 is a settler, 103 is an evaporator in step d), 104 is a separator in step e), 105 is an isolation column of the target α-olefin, 106—an isolation column of the recurrent solvent.

According to the presented method, the initial olefin, preferably ethylene, the solvent and the catalyst system (1) are fed into the oligomerization reactor 101. Next, the reaction mass (2) obtained during the oligomerization reaction and leaving the oligomerization reactor is brought into the contact with the deactivating agent of the catalyst system (3) to obtain a reaction mass containing the catalyst system residues. After that, the reaction mass containing the catalyst system residues enters the settler 102, in which the fraction containing the initial olefin (4) is isolated, to form a stream of oligomerization reaction products (5). The fraction containing the initial olefin (4) is optionally recycled to the oligomerization reactor. Next, the stream of the oligomerization reaction products (5) is fed into the evaporator 103, wherein the stream of the oligomerization reaction products is separated into a fraction of the target α-olefin (6), in particular predominantly containing C6+, and fraction (7) containing a by-product polymer and the catalyst system residues. After that, the fraction of the target α-olefin (6) predominantly containing C6+ is fed into the separation apparatus 104 for the separation into three fractions: the C2-C4 fraction (8), the C6+ fraction (11) and the C8+ fraction (streams (9) and/or (10)). The C8+ fraction (9), together with the C6+ fraction (11), is then directed to the isolation step of the target α-olefin (12) in 105, or the C8+ fraction (10) together with the C6+ fraction (11) is directed to the isolation step of the target α-olefin (12) in 105 and the C8+ fraction (10) is fed into the evaporator 103. The bottom product (13) remained after the isolation of the target α-olefin (12) is directed to the isolation step of the solvent in 106 to obtain a recurrent solvent (14) and a bottom product (15) containing the C8+ fraction.

Figure 2:
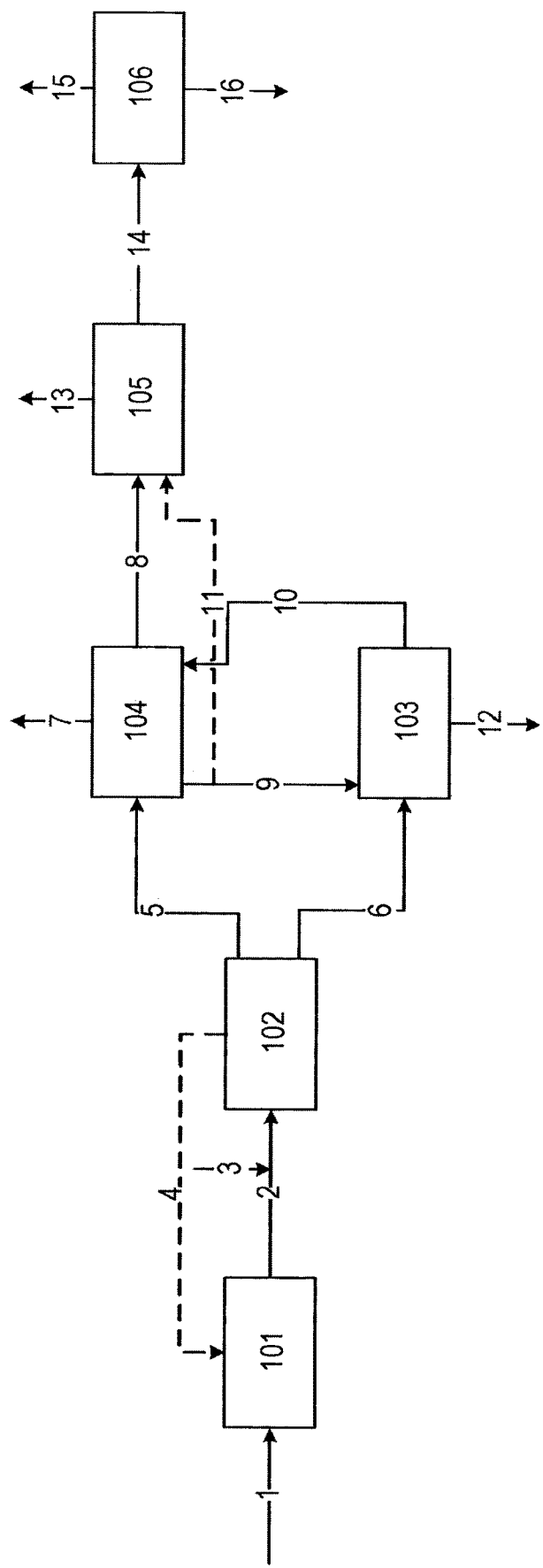

The second embodiment of the present invention is explained in more detail in FIG. 2, which presents a flowchart of the olefin oligomerization process with the implementation of the method of separating the oligomerization products according to the second embodiment of the present invention. In accordance with FIG. 2, 101 is an oligomerization reactor, 102 is a settler, 103 is an evaporator in step d), 104 is a separator in step e), 105 is an isolation column of the target α-olefin, 106—an isolation column of the recurrent solvent.

According to the presented method, the initial olefin (preferably ethylene), the solvent and the catalyst system (1) are fed into the oligomerization reactor 101. Next, the reaction mass (2) obtained during the oligomerization reaction and leaving the oligomerization reactor is brought into the contact with the deactivating agent of the catalyst system (3) to obtain a reaction mass containing the catalyst system residues. After that, the reaction mass containing the catalyst system residues enters the settler 102, in which the fraction containing the initial olefin (4) is isolated, to form a stream of oligomerization reaction products that is separated into two streams (5) and (6). The fraction containing the initial olefin (4) is optionally returned to the oligomerization reactor. Next, the first part of the stream of the oligomerization reaction products (5) is fed into the separator 104 to separate it into three fractions: C2-C4 fraction (7), C6+ fraction (8) and C8+ fraction (9). The second part of the stream of the oligomerization reaction products is fed into the evaporator 103, wherein the stream of the oligomerization reaction products is separated into a fraction of the target α-olefin (10) predominantly containing C6+, and a fraction (12) containing a by-product polymer and the catalyst system residues. After that, the fraction of the target α-olefin (10) predominantly containing C6+ is fed into the separator 104 for the separation into three fractions: the C2-C4 fraction (7), the C6+ fraction (8) and the C8+ fraction (streams (9) and/or (11)). The C8+ fraction (11), together with the C6+ fraction (8), is then directed to the isolation step of the target α-olefin (13) in 105 or together with the C6+ fraction (8) is directed to the isolation step of the target α-olefin (13) in 105 and the C8+ fraction (9) is fed into the evaporator 103. The bottom product (14) remained after the isolation of the target α-olefin (13) is directed to the isolation step of the solvent in 106 to obtain a recurrent solvent (15) and a bottom product (16) containing the C8+ fraction.

Schemes presented in FIG. 1 and FIG. 2 are examples of the present invention embodiments, and do not limit it.

This invention is more specifically described with the reference to the examples below. These examples are given only to illustrate the present invention and do not limit it.

Embodiment of the Invention

Solvent—cyclohexane
Catalyst System:
1) chromium source—chromium (III) 2-ethylhexanoate,
2) ligand—2,5-dimethylpyrrole,
3) alkylaluminum—the mixture of triethylaluminum and diethylaluminum chloride.

The catalyst system deactivating agent is 2-ethylhexanol.

Example 1. The separation of the stream of the ethylene oligomerization reaction products according to the first embodiment.

Cyclohexane preheated to a temperature of 90° C., ethylene preheated to a temperature of 70° C., and a catalyst system enter the oligomerization reactor operating at a pressure of 25 atm by means of metering pumps.

The oligomerization process of ethylene to hexene-1 is carried out at a temperature of 100-120° C. and a pressure of 25 atm to the ethylene conversion degree of approximately 50%. This reaction is exothermic and requires the use of the oligomerization reactor cooling system.

The reactor is a vertical heat exchanger with embedded tube bundles in a quantity necessary to withdraw the heat of the trimerization reaction. A coolant is fed into the shell side of the reactor. The gas mainly consisting of ethylene is separated from a liquid reaction mass, is discharged through a separate pipe stub located at the top of the separation part of the reactor, and enters the heat exchanger, where it is cooled with the coolant and partially condenses.

Next, the liquid reaction mass is fed through two collectors by gravity into a settler designed for the partial separation of unreacted ethylene and hydrogen.

In order to deactivate the catalyst system after the oligomerization reaction, the catalyst system deactivating agent and 2-ethylhexanol are fed by metering pumps into a manifold after the reactor before the reaction mass enters the settler.

In the settler the unreacted ethylene is discharged, it is recycled to the oligomerization reactor through a compression unit. The reaction mass containing the catalyst system residues enters the rotary film evaporator, where the by-product polymer, in particular polyethylene, the catalyst system residues, and the catalyst system deactivating agent are separated. The rotary film evaporator operates at a temperature of 150° C. and a pressure of from 0.05 to 0.1 atm.

The reaction mass from the rotary film evaporator purified from the by-product polymer, in particular, polyethylene, the catalyst system residues and the catalyst system deactivating agent enters an evaporation column. The evaporation column operates at a temperature of from 64° C. to 140° C. and a pressure of 3.5 atm gauge.

In the evaporation column, the reaction mass is separated into three streams:
  C2-C4 fraction;
  C6+ fraction that is brought to the isolation step of hexene-1;
  C8+ fraction partially returned to the rotary film evaporator and partially directed to the isolation step of the target product.

The isolation of hexene-1 is carried out in the packed distillation column at a temperature from 70 to 100° C. and a pressure of 2 atm gauge.

Next, the C6+ fraction remained after the isolation of hexene-1 is fed into the isolation step of a recurrent solvent.

The isolation step of the recurrent solvent is carried out in the packed distillation column at a temperature of from 80 to 140° C. and a pressure of 2 atm gauge.

Compositions of the streams are presented in Table 1.

Example 2. The separation of the stream of the ethylene oligomerization reaction products according to the second embodiment.

Cyclohexane preheated to a temperature of 90° C., ethylene preheated to a temperature of 70° C., and a catalyst system enter the oligomerization reactor operating at a pressure of 25 atm by means of metering pumps.

The oligomerization process of ethylene to hexene-1 is carried out at a temperature of 100-120° C. and a pressure of 25 atm to the ethylene conversion degree of approximately 50%. This reaction is exothermic and requires the use of the oligomerization reactor cooling system.

The reactor is a vertical heat exchanger with embedded tube bundles in a quantity necessary to withdraw the heat of the trimerization reaction. A coolant is fed into the shell space of the reactor. The gas mainly consisting of ethylene is separated from a liquid reaction mass, is discharged through a separate pipe stub located at the top of the separation part of the reactor, and enters the heat exchanger, where it is cooled with the coolant and partially condenses.

Next, the reaction mass is fed through two collectors by gravity into a settler designed for the partial separation of unreacted ethylene and optionally hydrogen (when used).

In order to deactivate the catalyst system after the oligomerization reaction, the catalyst system deactivating agent, 2-ethylhexanol is fed by metering pumps into a manifold after the reactor before the reaction mass enters the settler.

In the settler the unreacted ethylene is discharged, it is recycled to the oligomerization reactor through a compression unit. Also in the settler, the by-product polymer and of the catalyst system residues are concentrated at the bottom of the apparatus, thus resulting in forming the clarified part of the reaction mass and the concentrated part of the reaction mass.

The clarified part of the reaction mass from the upper part of the settler enters the evaporation column. The evaporation column operates at a temperature of from 64° C. to 140° C. and a pressure of 3.5 atm gauge.

In the evaporation column, the reaction mass is separated into three streams:
C2-C4 fraction;
C6+ fraction that is brought to the isolation step of hexene-1;
C8+ fraction, which is partially returned to the rotary film evaporator and partially directed to the isolation step of the target product.

The isolation of hexene-1 is carried out in the packed distillation column at a temperature of from 70 to 100° C. and a pressure of 2 atm gauge.

Next, the C6+ fraction remained after the isolation of 1-hexene is fed to the isolation step of a recurrent solvent.

The isolation step of the recurrent solvent is carried out in the packed column at a temperature of from 80 to 140° C. and a pressure of 2 atm gauge.

The C8+ fraction is fed into the rotary film evaporator where the additional separation of the C8+ fraction occurs, and the C8+ fraction is returned to the evaporation column and further with a general stream of the C6+ fraction is brought to the isolation step of hexene-1. The rotary film evaporator operates at a temperature of 150° and a pressure form 0.05 to 0.1 atm.

The concentrated part of the reaction mass containing the by-product polymer and the catalyst system residues enters the rotary film evaporator, where the by-product polymer, in particular polyethylene, the catalyst system residues and the catalyst system deactivating agent are separated.

The reaction mass purified from the by-product polymer, in particular, polyethylene, the catalyst system residues and the catalyst system deactivating agent from the rotary film evaporator enters the evaporation column. The evaporation column operates at a temperature of from 64° C. to 140° C. and a pressure of 3.5 atm gauge.

Compositions of the streams are presented in Table 2.

When using the methods of separating the stream of the oligomerization reaction products, as outlined in Examples 1 and 2, the presence of the by-product polymer at the isolation step of the target product (see Table 1, a commercial hexene-1 stream (12) from apparatus 105 and Table 2, a commercial hexene-1 stream (13) from apparatus 105, the content of the by-product polymer is 0 wt. %) and at the isolation step of the recurrent solvent (Table 1, the recurrent solvent stream (14) from apparatus 106 and Table 2, the recurrent solvent stream (15) from apparatus 106, the content of the by-product polymer is 0 wt. %) is excluded; the maximum extraction of hexene-1 (the content of hexene-1 in the commercial hexene-1 stream (12) (see Table 1), and the content of hexene-1 in the commercial hexene-1 stream (13) (see Table 2) is 99.01% by weight) and the recurrent solvent (the cyclohexane content is 99.5 wt. %—in the recurrent solvent stream (14) (see Table 1), and—in the recurrent solvent stream (15) (see Table 2) from the reaction mass is ensured; the obtainment of the C8+ fraction purified from the catalyst system components and the by-product polymer (the content of the by-product polymer and the catalyst system residues is 0 wt. % in the C8+ fraction stream (15) (Table 1) and C8+ fraction stream (16) (Table 2)) is provided, which in turn allows the use of the C8+ fraction for washing the oligomerization reactor.

TABLE 1

Compositions of the streams according to Example 1.

| Components | Reaction mass (2) from 101 into 102 wt. % | Reaction mass (3) from 102 into 103 wt. % | Stream (11) from 104 into 105 wt. % | Stream (9) from 104 into 105 wt. % | Stream (6) from 103 into 104 wt. % | Commercial hexene-1 (12) from 105 wt. % | Stream (13) from 105 into 106 wt. % | Recurrent solvent (14) from 106 wt. % | C8+ (15) from 106 wt. % |
|---|---|---|---|---|---|---|---|---|---|
| hydrogen | 0.09 | 0.00 | 0.00 | 0.00 | 0.00 | 0.00 | 0.00 | 0.00 | 0.00 |
| ethylene | 34.07 | 6.30 | 0.19 | 0.00 | 6.30 | 0.00 | 0.00 | 0.00 | 0.00 |
| butene-1 | 0.04 | 0.04 | 0.01 | 0.00 | 0.04 | 0.00 | 0.00 | 0.00 | 0.00 |
| hexene-1 | 14.40 | 20.15 | 20.80 | 14.70 | 20.71 | 99.01 | 0.40 | 0.41 | 0.00 |
| cyclohexane | 49.37 | 70.56 | 77.40 | 80.79 | 72.06 | 0.32 | 96.91 | 99.50 | 0.05 |
| cis-2-hexene | 0.10 | 0.14 | 0.15 | 0.07 | 0.14 | 0.57 | 0.03 | 0.04 | 0.00 |
| trans-2-hexene | 0.02 | 0.02 | 0.02 | 0.01 | 0.02 | 0.10 | 0.01 | 0.01 | 0.00 |
| ethylbenzene | 0.24 | 0.35 | 0.36 | 0.90 | 0.22 | 0.00 | 0.45 | 0.03 | 16.28 |
| octene-1 | 0.01 | 0.02 | 0.02 | 0.03 | 0.01 | 0.00 | 0.02 | 0.02 | 0.13 |
| decenes | 0.98 | 1.42 | 1.00 | 2.50 | 0.40 | 0.00 | 1.72 | 0.00 | 77.67 |
| tetradecenes | 0.19 | 0.27 | 0.05 | 1.00 | 0.10 | 0.00 | 0.15 | 0.00 | 5.87 |
| the catalyst system residues | 0.08 | 0.12 | 0.00 | 0.00 | 0.00 | 0.00 | 0.00 | 0.00 | 0.00 |

TABLE 1-continued

Compositions of the streams according to Example 1.

| Components | Reaction mass (2) from 101 into 102 wt. % | Reaction mass (3) from 102 into 103 wt. % | Stream (11) from 104 into 105 wt. % | Stream (9) from 104 into 105 wt. % | Stream (6) from 103 into 104 wt. % | Commercial hexene-1 (12) from 105 wt. % | Stream (13) from 105 into 106 wt. % | Recurrent solvent (14) from 106 wt. % | C8+ (15) from 106 wt. % |
|---|---|---|---|---|---|---|---|---|---|
| 2-ethylhexanol | 0.43 | 0.62 | | 0.00 | 0.00 | 0.00 | 0.30 | 0.00 | 0.01 |
| By-product polymer | 0.00 | 0.00 | 0.00 | 0.00 | 0.00 | 0.00 | 0.00 | 0.00 | 0.00 |
| Total | 100 | 100 | 100 | 100 | 100 | 100 | 100 | 100 | 100 |
| Pressure, atm gauge | 23 | 4 | 2 | 2 | −0.2 | 2 | 1 | 3 | 1 |
| Temperature, ° C. | 99.1 | 83.6 | 116.5 | 116.5 | 162.1 | 40.0 | 96.6 | 89.9 | 60.0 |

TABLE 2

Compositions of the streams according to Example 2.

| Components | Reaction mass (2) from 101 into 102 wt. % | Reaction mass (5) from 102 into 104 wt. % | Stream (8) from 104 into 105 wt. % | Stream (9) from 104 into 103 wt. % | Stream (10) from 103 $_B$ into 104 wt. % | Stream (12) from 103 wt. % | Stream (8) into 105 wt. % | Commercial hexene-1 (13) from 105 wt. % | Stream (14) from 105 into 106 wt. % | Recurrent solvent (15) from 106 wt. % | C8+ (16) from 106 wt. % |
|---|---|---|---|---|---|---|---|---|---|---|---|
| hydrogen | 0.09 | 0.00 | 0.00 | 0.00 | 0.00 | 0.00 | 0.00 | 0.00 | 0.00 | 0.00 | 0.00 |
| ethylene | 34.07 | 6.30 | 0.19 | 0.04 | 0.03 | 0.00 | 0.19 | 0.00 | 0.00 | 0.00 | 0.00 |
| butene-1 | 0.04 | 0.04 | 0.01 | 0.00 | 0.00 | 0.00 | 0.01 | 0.00 | 0.00 | 0.00 | 0.00 |
| hexene-1 | 14.40 | 20.15 | 20.54 | 9.47 | 14.64 | 0.00 | 21.39 | 99.01 | 0.40 | 0.41 | 0.00 |
| cyclohexane | 49.37 | 70.56 | 76.98 | 52.86 | 83.07 | 0.00 | 76.16 | 0.32 | 96.91 | 99.50 | 0.05 |
| cis-2-hexene | 0.10 | 0.14 | 0.15 | 0.07 | 0.07 | 0.07 | 0.15 | 0.57 | 0.03 | 0.04 | 0.00 |
| trans-2-hexene | 0.02 | 0.02 | 0.02 | 0.01 | 0.01 | 0.01 | 0.02 | 0.10 | 0.01 | 0.01 | 0.00 |
| ethylebenzene | 0.24 | 0.35 | 0.36 | 0.90 | 0.31 | 1.93 | 0.36 | 0.00 | 0.45 | 0.03 | 16.28 |
| octene-1 | 0.01 | 0.02 | 0.02 | 0.03 | 0.01 | 0.05 | 0.02 | 0.00 | 0.02 | 0.02 | 0.13 |
| decenes | 0.98 | 1.42 | 1.37 | 7.85 | 1.32 | 19.36 | 1.35 | 0.00 | 1.72 | 0.00 | 77.67 |
| tetradecenes | 0.19 | 0.27 | 0.12 | 6.85 | 0.37 | 18.31 | 0.12 | 0.00 | 0.15 | 0.00 | 5.87 |
| the catalyst system residues | 0.08 | 0.12 | 0.00 | 4.88 | 0.00 | 8.03 | 0.00 | 0.00 | 0.00 | 0.00 | 0.00 |
| 2-ethylhexanol | 0.43 | 0.62 | 0.24 | 16.83 | 0.14 | 46.22 | 0.24 | 0.00 | 0.30 | 0.00 | 0.01 |
| By-product polymer | 0.00 | 0.00 | 0.00 | 0.21 | 0.00 | 0.57 | 0.00 | 0.00 | 0.00 | 0.00 | 0.00 |
| Total | 100 | 100 | 100 | 100 | 100 | 100 | 100 | 100 | 100 | 100 | 100 |
| Pressure atm gauge | 23 | 4 | 4 | 4 | 3 | −0.2 | 2 | 2 | 1 | 3 | 1 |
| Temperature, ° C. | 99.1 | 83.6 | 127.5 | 145.7 | 66.4 | 162.1 | 116.5 | 40.0 | 96.6 | 89.9 | 60.0 |

Example 3 (comparative). The separation of the stream of the ethylene oligomerization reaction products without the use of step d)

Figure 3:
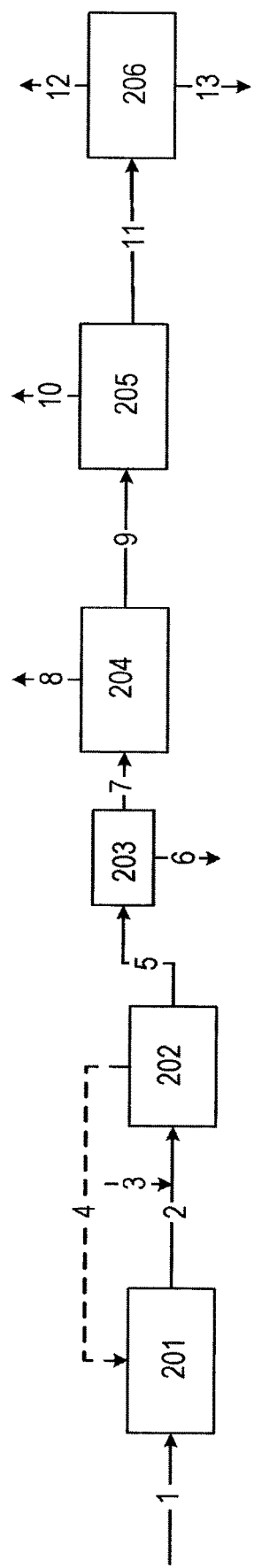

The sequence of steps according to the Example 3 is presented in detail in FIG. 3.

Cyclohexane preheated to a temperature of 90° C., ethylene preheated to a temperature of 70° C., and a catalyst system are fed to (1) the oligomerization reactor (201) operating at a pressure of 25 atm by means of dosing pumps.

The oligomerization process of ethylene in hexene-1 is carried out at a temperature of 100-120° C. and a pressure of 25 atm to the ethylene conversion degree of approximately 50%. This reaction is exothermic and requires the use of the oligomerization reactor cooling system.

The reactors are vertical heat exchangers with embedded tube bundles in a quantity necessary to withdraw the heat of the trimerization reaction. A coolant is fed into the shell space of the reactors. The gas mainly consisting of ethylene is separated from a liquid reaction mass, is discharged through a separate pipe stub located at the top of the separation part of the reactors, and is brought to the heat exchanger, where it is cooled with the coolant and partially condenses.

Next, the reaction mass (2) is fed through two collectors by gravity into a settler (202) designed for the partial separation of unreacted ethylene (4) and optionally hydrogen (when used).

In order to deactivate the catalyst system after the oligomerization reaction, the catalyst system deactivating agent, 2-ethylhexanol is fed by metering pumps into a manifold after the reactors before the reaction mass enters the settler.

The reaction mass (5) containing the catalyst system residues enters a filtration system (203) to separate the by-product polymer and the catalyst system residues.

After passing the filtration system, the reaction mass (7) enters a distillation column (204). The distillation column is designed to isolate ethylene and hydrogen (8) from the reaction mass.

Further, the reaction mass (9) purified from ethylene and hydrogen from the bottom part of the distillation column is fed into the distillation column (205) for isolating the target product, namely hexene-1. The isolation of hexene-1 is performed in the packed distillation column at a temperature of from 70 to 100° C. and a pressure of 2 atm gauge. In the upper part of the column, hexene-1 (10) is isolated, the bottom product (11) enters the distillation column (206) for isolating a recurrent solvent (12). The isolation step of the recurrent solvent is carried out in the packed distillation column at a temperature of from 80 to 140° C. and a pressure of 2 atm gauge.

At the same time, at the plant start-up, the deposition of the by-product polymer on the equipment walls occurs almost immediately, including distillation columns and their elements, and the sharp reduction in the efficiency of the operation of columns occurs, which does not allow to obtain reliable data on the compositions of the streams and the quality of the equipment operation.

Thus, due to the insufficient residence time of the reaction mass with the dissolved by-product polymer in the settler, the great part of the by-product polymer (up to 0.5 wt. % of the mass of the entire stream) enters the ethylene and hydrogen isolation column, and further into columns of isolating hexene-1 and the recurrent solvent, resulting in periodic shutdowns of pumping equipment due to clogging with the by-product polymer (1 or more times per day). The part of the by-product polymer also enters the packed section of the distillation column, precipitates on the surface of the packing elements, thus resulting in the sharp decrease in the separation efficiency of the reaction mass, so that it is possible to either isolate the recurrent solvent of the desired quality by reducing the product quality up to 20%, or isolate the target product of the desired quality and the solvent containing up to 20% of the product, and also resulting in the reduction of the distillation column productivity for up to 50%.

The invention claimed is:

1. A method of separating olefin oligomerization products, the method comprising the following sequence of steps:
    a) discharging a reaction mass from an oligomerization reactor;
    b) contacting the reaction mass with a catalyst system deactivating agent;
    c) isolating a fraction comprising an initial olefin from the reaction mass to form a stream of the fraction comprising the initial olefin and an oligomerization reaction product stream;
    c)* directing a first part of the oligomerization reaction product stream from step c) into a separation column; and directing a second part of the oligomerization reaction product stream from step c) to an evaporator in step d);
    d)* separating the first part of the oligomerization reaction product stream from step c) in the separation column into a light fraction, a fraction of a target α-olefin, and a heavy fraction of oligomers, followed by directing the heavy fraction of oligomers to the evaporator in(step d);
    d) separating, in the evaporator, the heavy fraction of oligomers from step d)* and the second part of the oligomerization reaction product stream into a fraction predominantly comprising the target α-olefin, and a fraction comprising a by-product polymer and catalyst system residues;
    e) directing the fraction predominantly comprising the target α-olefin obtained in step d) and the first part of the oligomerization reaction product stream from step c) into the separation column, for the separating in step d)* into the light fraction, the fraction of the target α-olefin, and the heavy fraction of oligomers.

2. The method according to claim 1, characterized in that ethylene is used as the initial olefin.

3. The method according to claim 1, characterized in that the oligomerization rector is used for trimerization of the initial olefin.

4. The method according to claim 3, characterized in that the oligomerization rector is used for trimerization of ethylene.

5. The method according to claim 4, characterized in that the fraction predominantly comprising the target α-olefin is a C6+ fraction.

6. The method according to claim 4, characterized in that the light fraction is a C2-C4 fraction.

7. The method according to claim 4, characterized in that the heavy fraction of oligomers is a C8+ fraction.

8. The method according to claim 1, characterized in that the fraction if the target α-olefin obtained in step e) comprises hexene-1.

9. The method according to claim 1, characterized in that hexene-1 is isolated from the fraction of the target α-olefin obtained in step e).

10. The method according to claim 1, characterized in that part of the heavy fraction of oligomers is directed to a step of isolating the target α-olefin.

11. The method according to claim 1, characterized in that the fraction comprising an initial olefin isolated in step c) is returned into the oligomerization reactor.

12. The method according to claim 1, characterized in that the fraction of the target α-olefin obtained in step d)* is fed to a step of isolating the target α-olefin.

13. The method according to claim 12, characterized in that the step of isolating the target α-olefin provides a bottom product that is separated into a solvent fraction and a fraction of oligomers.

14. The method according to claim 1, characterized in that the evaporator is a thin-film evaporator or a rotary film evaporator.

15. The method according to claim 14, characterized in that the evaporator is the rotary film evaporator.

16. The method according to claim 1, characterized in that the step d)* and step e) are carried out together.

17. The method according to claim 1, characterized in that the step d) is carried out at a temperature of from 64 to 175° C.

18. The method according to claim 1, characterized in that the step d) is carried out at a temperature of from 80 to 150° C.

19. The method according to claim 1, characterized in that the step d) is carried out at a pressure of from 0 to 6 atm gauge.

20. The method according to claim 19, characterized in that the step d) is carried out at a pressure of from 0 to 3 atm gauge.

21. The method according to claim 19, characterized in that the step d) is carried out at a pressure of from 0 to 2 atm gauge.

\* \* \* \* \*